US012029920B2

(12) United States Patent
Bondar et al.

(10) Patent No.: US 12,029,920 B2
(45) Date of Patent: Jul. 9, 2024

(54) AUTOMATED QUALITATIVE DESCRIPTION OF ANATOMICAL CHANGES IN RADIOTHERAPY

(71) Applicant: KONINKLIJKE PHILIPS N.V., Eindhoven (NL)

(72) Inventors: Maria Luiza Bondar, Waalre (NL); Matthieu Frédéric Bal, Geldrop (NL); Alfonso Agatino Isola, Eindhoven (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 432 days.

(21) Appl. No.: 17/413,539

(22) PCT Filed: Dec. 11, 2019

(86) PCT No.: PCT/EP2019/084558
§ 371 (c)(1),
(2) Date: Jun. 12, 2021

(87) PCT Pub. No.: WO2020/120531
PCT Pub. Date: Jun. 18, 2020

(65) Prior Publication Data
US 2022/0054861 A1 Feb. 24, 2022

(30) Foreign Application Priority Data
Dec. 14, 2018 (EP) .................... 18212534

(51) Int. Cl.
*A61N 5/10* (2006.01)
(52) U.S. Cl.
CPC .... *A61N 5/1049* (2013.01); *A61N 2005/1074* (2013.01)

(58) Field of Classification Search
CPC .............. A61N 5/1049; A61N 2005/1074
See application file for complete search history.

(56) References Cited

U.S. PATENT DOCUMENTS 9,600,922 B2 3/2017 Tsukagoshi
9,764,162 B1 9/2017 Willcut
(Continued)

FOREIGN PATENT DOCUMENTS

JP 2012024145 A 2/2012

OTHER PUBLICATIONS

International Search Report and Written Opinion of PCT/EP2019/084558, dated Feb. 28, 2020.
(Continued)

*Primary Examiner* — Mark R Gaworecki

(57) ABSTRACT

A system and a method for monitoring anatomical changes in a subject in radiation therapy are provided, as well as an arrangement for medical imaging and analysis and a computer program product for carrying out the method. For monitoring anatomical changes in a subject in radiation therapy, the following steps are performed. First anatomical image data and subsequent anatomical image data of the subject are received. The first anatomical image data and the subsequent anatomical image data are analyzed. This analysis comprises registering the subsequent anatomical data to the first anatomical data. Changes between the first anatomical image data and the subsequent anatomical image data are identified as change states, and the identified change states are matched to corresponding qualitative descriptions. A monitoring report is provided, which comprises the qualitative descriptions of the identified changes.

21 Claims, 4 Drawing Sheets

(56) References Cited

U.S. PATENT DOCUMENTS

| | | | |
|---|---|---|---|
| 9,795,806 | B2 | 10/2017 | Matsuzaki |
| 9,865,048 | B2 | 1/2018 | Wakai |
| 10,022,560 | B2 | 7/2018 | Kumar |
| 10,456,595 | B2 | 10/2019 | Ribbing |
| 10,638,989 | B2 | 5/2020 | Van Beek |
| 2010/0111396 | A1 | 5/2010 | Boucheron |
| 2012/0207372 | A1 | 8/2012 | Ishihashi |
| 2016/0263399 | A1 | 9/2016 | Matsuzaki |
| 2017/0091574 | A1 | 3/2017 | Udupa |
| 2017/0340901 | A1* | 11/2017 | Haas .................. G06T 7/149 |

OTHER PUBLICATIONS

Boch, Isabelle "Mathematical Morphology on Bipolar Fuzzy Sets: General Algebraic Framework", International Journal of Approximate Reasoning, vol. 53, 2012, pp. 1031-1060.

Surucu, Murat et al "Decision Trees Predicting TUmor Shrinkage for Head and Neck Cancer: Implications for Adaptive Radiotherapy", Radiotherapy, vol. 15, No. 1, 2015, pp. 139-145.

Mohan, Vineet "Correlating Scored Daily Anatomical Changes to Invivo EPID Dosimetry and Cone Beam CT Based Dose Calculations", Tu Delft University, 2017.

Zegers, Catharina M.L. et al, "Three-dimensional dose evaluation in breast cancer patients to define decision criteria for adaptive radiotherapy," ACTA Oncologica, vol. 56, No. 11, pp. 1487-1494, Nov. 2017

Moratz, Reinhard et al "Qualitative spatial reasoning about relative point position", Journal of Visual Languages and Computing, vol. 19, 2008, pp. 75-98.

Zhou, Zhengdong et al, "An effective calculation method for an overlap volume histogram descriptor and its application in IMRT plan retrieval," European Journal of Medical Physics, vol. 32, No. 10, pp. 1339-1343, Oct. 2016.—Abstract Only.

Li, Sanjiang et al "Region Connection Calculus: Its models and composition table," Artificial Intelligence, vol. 145, pp. 121-146, Apr. 2003.

Sabharwal, Chaman L. et al "Modeling Cardinal Direction Relations in 3D for Qualitative Spatial Reasoning," Mining Intelligence and Knowledge Exploration, 2014, pp. 199-214. Abstract Only.

Skiadopoulos, Spiros, et al, "Composing cardinal direction relations," Artificial Intelligence, vol. 152, No. 2, pp. 143-171, Feb. 2004.

Dylia, Frank et al "A Survey of Qualitative Spatial and Temporal Calculi—Algebraic and Computational Properties", ACM Computing Surveys, vol. V, 2016.

* cited by examiner

AUTOMATED QUALITATIVE DESCRIPTION OF ANATOMICAL CHANGES IN RADIOTHERAPY

CROSS REFERENCE TO RELATED APPLICATIONS

This application is the U.S. National Phase application under 35 U.S.C. § 371 of International Application No. PCT/EP2019/067512 filed Jul. 1, 2019, which claims the benefit of European Patent Application Number 18181695.0 filed Jul. 4, 2018. International Application No. PCT/EP2019/067512 and European Patent Application Number 18181695.0 are hereby incorporated by reference herein.

FIELD OF THE INVENTION

The invention generally relates to the monitoring of anatomical changes, and in particular, but not exclusively, the invention relates to automated monitoring of anatomical changes in subjects undergoing radiation therapy.

BACKGROUND OF THE INVENTION

In radiation therapy, target structures in patient's bodies, such as tumors, are treated by subjecting them to radiation. The radiation can be in the form of external radiation such as photons, or particles such as protons, for example in external beam radiotherapy (EBRT). The treatment is delivered in such a way that the radiation that is delivered to the target structures (TSs) is as high as possible, while at the same time the radiation delivered to the surrounding healthy, tissue and structures, usually referred to as organs at risk (OARs), is as low as possible.

During the therapy, the dose of radiation is usually delivered to the patient over several radiation therapy sessions, with a recovery period between each session. Tis approach is known as fractionated radiation therapy, and the sessions are referred to as fractions. The reasoning behind this approach is that TS tumor tissue is expected to recover less well from a dose fraction than the healthy tissue including the OARs.

Fractions are often delivered on a daily basis, resulting in a treatment that is spread out in time. Over this time period, the patient may have anatomical changes such as organ movements and deformations that occur naturally in the body. Each fraction of the therapy that is delivered to a patient can also impact the anatomy. In particular, during radiation therapy, it is expected that target structures such as tumors will shrink. In the current context "during" radiation therapy means in the full time span during which all the therapy fractions are delivered including the recovery period, not the specific point in time when the patient is actually being subjected to the radiation "During", or "in" radiation therapy is an indication of the context wherein anatomical changes take place, but monitoring of the changes takes place before or after delivery of a therapy fraction, but not during actual delivery of the fraction. The anatomical changes that occur in patients during the treatment need to be monitored and assessed to ensure the treatment progresses properly and that changes can be made or extra measures taken when needed.

In the current clinical practice of radiation therapy, anatomical changes that occur in patients during radiation therapy are monitored and recorded in a treatment log. Qualitative descriptions are used to describe, communicate and record these changes as well as quantitative measurements. Typically, these changes assessed visually and recorded manually. Typically, visual inspection involves manual processing of quantitative measurements, and comparison of the treatment planning image, such as a CT scan, and an in-room acquired image such as a cone-beam CT (CBCT) image or planar x-ray image, or a separately recorded MRI image. The in-room images are usually taken immediately prior to delivery of a treatment fraction and used for both status monitoring and patient setup.

Based on this visual assessment and analysis of quantitative data, the clinician interprets and describes the type of anatomical changes qualitatively. However, visual assessment, manual processing and interpretation are error prone and time consuming. Errors can occur, because the clinician may overlook anatomical changes that are relevant, or can erroneously interpret the spatial relationships between objects in different images. Also, manual entry of qualitative descriptions can lead to variations in description of similar situations, which can introduce inconsistencies. In addition, interpretation of anatomical changes requires the analysis of large amounts of data and specialized skills.

SUMMARY OF THE INVENTION

The current invention seeks to provide an automated method for monitoring anatomical changes in a subject undergoing radiation therapy. The current invention further seeks to address the need for consistent, qualitative descriptions of changes in the subject's anatomy during the course of treatment.

Thereto a system and a method for monitoring anatomical changes in a subject in radiation therapy are provided, as well as an arrangement for medical imaging and analysis and a computer program product for carrying out the method.

The system for monitoring anatomical changes in a subject in radiation therapy comprises an analysis unit comprising an input configured to receive first anatomical image data and subsequent anatomical image data of the subject, which analysis unit is at least configured to register the subsequent anatomical data to the first anatomical data. The system further comprises a change state identification unit configured to identify changes between the first anatomical image data and the subsequent anatomical image data as change states, and a qualitative translator configured to match the identified change states to corresponding qualitative descriptions. Change states are a number of predefined categories wherein changes are grouped according to their characteristics. A change state is identified by assigning the category that best corresponds to the characteristics of the change between the first anatomical image data and the subsequent anatomical image data. Preferably, the qualitative descriptions provide an indication of the characteristics of the change state. More preferably, the qualitative descriptions reflect how a physician would describe the characteristics of the change when monitoring the patient during treatment. The system also comprises a reporting unit configured to provide a monitoring report comprising qualitative descriptions of the identified change states. The corresponding qualitative descriptions can, for example, be natural language descriptions and/or graphic images, preferably in the form of pictograms. Pictograms have the advantage of being easily understandable not only by the clinician himself, but also by e.g. the patient or a consulting physician from a different field of medicine.

In an embodiment of the system, the change state identification unit comprises at least one qualitative spatial reasoning algorithm, which qualitative spatial reasoning algorithm is preferably an RCC-8 calculus algorithm and/or a Cardinal spatial reasoning algorithm.

Preferably, the analysis unit of the system further comprises an input configured to receive dose distribution data of a treatment plan of the subject, and the change state identification unit is additionally or alternatively configured to identify changes between the dose distribution data and subsequent anatomical image data as change states. By including this optional input, the system can additionally or alternatively monitor anatomical changes in the subject as compared to the planned dose distribution.

Preferably, the qualitative translator is configured to match the identified change states to the corresponding description by using a look-up table.

Preferably, the reporting unit comprises a display for visually displaying the monitoring report. This is preferred in particular, when the monitoring report is a pictographic report. It is particularly advantageous for the display to be configured to visually display the monitoring report in the form of a graphical user interface. An advantage of presenting the report in the form of a user interface is that a version of the report can be selected and displayed that is most suitable to the situation. A further advantage is that additional data, for example the images acquired of the patient, dosimetric information or quantitative data obtained from further analysis, can be available in the background and selected and displayed when appropriate or necessary. When not selected, the information is not displayed, thereby simplifying the main view of the report, and making this easier to understand. Preferably, in order to make optimal use of these options, the graphical user interface comprises at least one control for selecting the information to be displayed as part of the monitoring report.

The method for monitoring anatomical changes in a subject in radiation therapy comprises a step of receiving first anatomical image data and subsequent anatomical image data of the subject, and a step of analyzing the first anatomical image data and the subsequent anatomical image data, wherein the step of analyzing comprises registering the subsequent anatomical data to the first anatomical data. The method further comprises a step of identifying changes between the first anatomical image data and the subsequent anatomical image data as change states, and a step of matching the identified change states to corresponding qualitative descriptions. The method also comprises a step of providing a monitoring report comprising qualitative descriptions of the identified changes. The method is preferably computer implemented.

In a preferred embodiment of the method, the step of identifying changes comprises supplying the first anatomical image data and the subsequent anatomical image data to at least one qualitative spatial reasoning algorithm, which qualitative spatial reasoning algorithm is preferably an RCC-8 calculus algorithm and/or a Cardinal spatial reasoning algorithm.

Preferably, the step of receiving first and subsequent anatomical image data of the subject further comprises receiving dose distribution data of a treatment plan of the subject, and the step of identifying changes additionally or alternatively comprises identifying changes between the dose distribution data and subsequent anatomical image data as change states.

In another preferred embodiment, that may be combined with other embodiments and preferences, the method step of analyzing the anatomical image data further comprises obtaining quantitative image data, which quantitative image data preferably comprises at least one of a region of interest size, a region of interest size change, the distance a region of interest has shifted, the total radiation dose a region of interest has received. When quantitative image data is obtained, the monitoring report preferably also comprises at least one quantitative description of at least one of the identified changes.

The arrangement for medical imaging and analysis comprises one or more imaging devices configured to provide images of a subject to be treated, a contouring tool configured to provide anatomical image data based on the images provided by the one or more imaging devices, and the system as described above for monitoring anatomical changes in radiation therapy.

An advantage of the current invention is that anatomical changes in patients undergoing radiation therapy can be monitored faster and more accurately. The identification of the changes as change states allows for consistent categorization of changes. The automated analysis of the first and subsequent images in combination with the automated identification of changes is faster more accurate than manual comparison of the images by a clinician.

Another advantage of the current invention is that anatomical changes in patients undergoing radiation therapy can be monitored more consistently. The identification of the changes as change states allows for consistent categorization of changes. Also, each change state is matched to a corresponding qualitative description. As a result, the changes that belong to the same category will have the same qualitative description. This has the further advantage that it is easier for a physician or clinician to find similar cases in a database. This can also have the further advantage that the dataset may be used as input for machine learning algorithms.

A further advantage lies in that a monitoring report is presented that provides direct insight in changes without requiring further analysis. Because the changes are reported in a qualitative manner, for example by using language that is similar to that used by physicians when describing a patient's status, the report can be read or shown to a patient or consulting physician for providing information without requiring extensive explanations of the data.

Further advantages from the described invention will also be apparent to the skilled person.

DETAILED DESCRIPTION OF THE INVENTION

Figure 1:
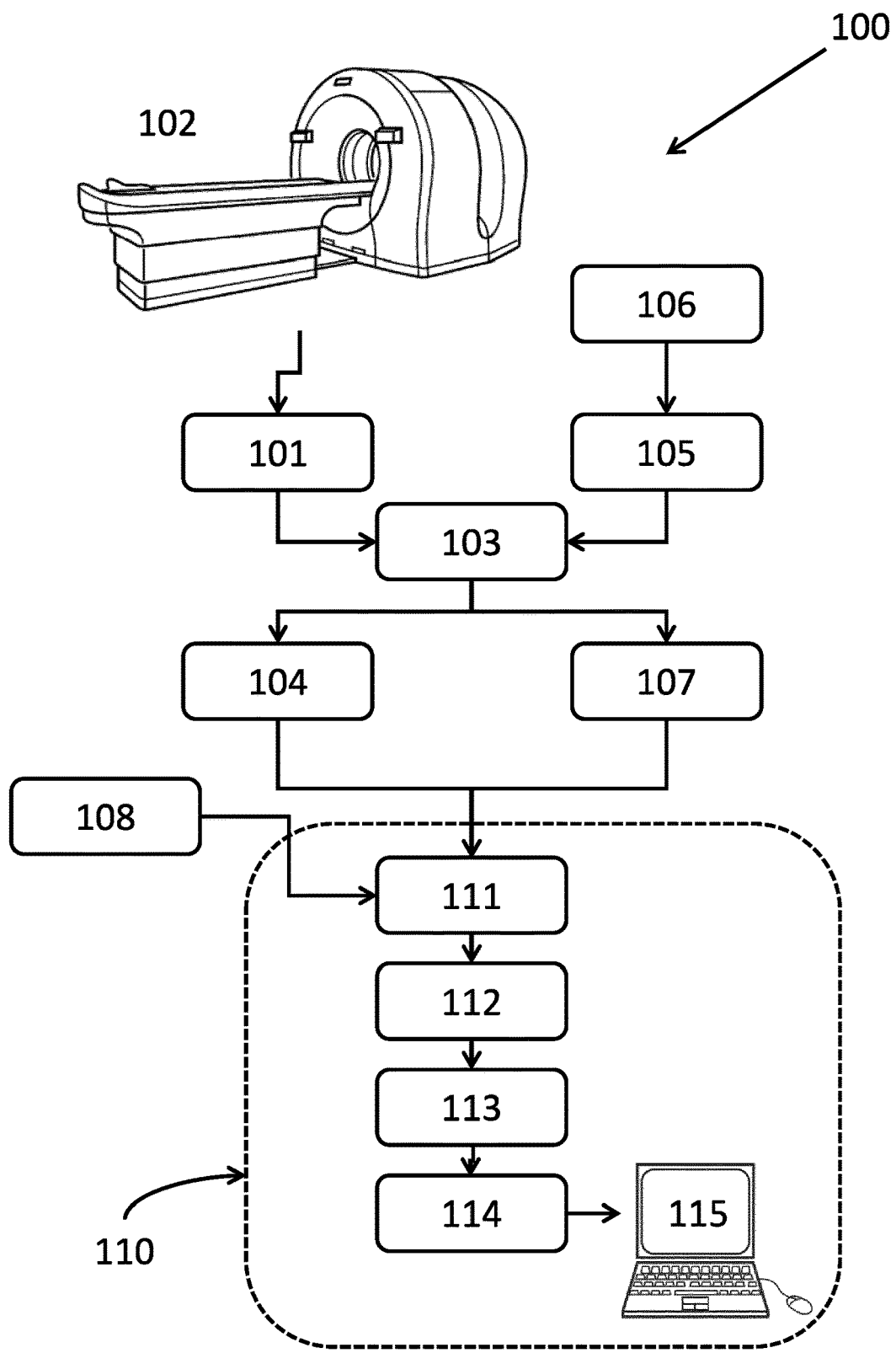
FIG. 1 schematically and exemplarily illustrates a system for monitoring anatomical changes in a subject in radiation therapy and further components of an arrangement for medical imaging and analysis.

FIG. 1 illustrates a system for monitoring anatomical changes 110 in a subject in radiation therapy. In this example, the system is illustrated as part of an arrangement 100 for medical imaging and analysis.

In the arrangement 100, a planning image 101 is acquired of the subject to be treated by an imaging device 102. The image can be a computed tomography image (CT), magnetic resonance image (MR), positron emission tomography (PET) image, another medical image, or a combined image, such as a combined PET/CT or PET/MR image. In FIG. 1, as an example, the imaging device 102 is a PET/CT imaging device. The regions of interest (ROIs) are delineated in this first image using a contouring tool 103 to provide first anatomical image data 104. The ROIs in the subject will comprise at least one target structure (TS), normally a tumor, but may also include one or more organs at risk (OARS). A contouring tool commonly interacts with the user, who can be for example a trained medical imaging technician or a radiologist, to define the contours of the ROIs. This process can be completely manual, or partly or fully automated.

During the course of treatment, at least one subsequent image 105 of the subject is acquired. This image may be acquired with the same imaging device 102 as the planning image, but can also be acquired using one or more alternative imaging devices 106. Such an alternative imaging device can be CT, MR or other medical imaging device. In a preferred embodiment, the subsequent image is acquired using the alternative medical imaging device 106 that is either a cone-beam CT (CBCT) or planar x-ray imaging device configured to image the subject in the treatment room. The advantage of this setup is that the image can be used for monitoring of anatomical changes in the subject as well as setup of the subject for delivery of the radiation therapy treatment fraction.

In the subsequent image 105 the ROIs are also delineated using the contouring tool 103 to provide subsequent anatomical image data 107. Contouring can be done from scratch, as in the planning image, manually, automatically, or semi-automatically, with user interaction. Contouring of the subsequent image can also be done by automatically propagating the contours from the planning image 101 to the subsequent image 105 by using the process of deformable image registration. When this process is used, the user preferably has the option of approving and/or manually correcting the automatically propagated contours.

Next, the first anatomical image data 104 and the subsequent anatomical image data 107 are analyzed in order to monitor anatomical changes in the subject. This is done using a system for monitoring anatomical changes 110 in radiation therapy. The system comprises an analysis unit 111, a change state identification unit 112, a qualitative translator 113 and a reporting unit 114. The analysis unit 111 comprises an input configured to receive the first anatomical image data 104 and the subsequent anatomical image data 107 of the subject.

The analysis unit 11I is at least configured to register the subsequent anatomical image data 107 to the first anatomical image data 104. As explained above, the first, planning image 101 may be acquired using a different imaging device 102 from the alternative medical imaging device 106 used for acquisition of the subsequent image 105. Also, the position of the subject in an imaging device will vary slightly for each acquisition of an image. As a result, the frame of reference for the anatomical image data can vary for each image as well as the scale. However, in order to make an accurate and reliable comparison, both the first anatomical image data 104 and the subsequent anatomical image data 107 should have the same frame of reference. To be able to detect changes that are due to changes in the subject's anatomy and not the circumstances under which the image was acquired, the images should have the same scale in size and ha % e the same coordinate system. For this purpose, the subsequent image and its anatomical image data, need to be matched to the first anatomical image and its anatomical image data in scale and frame of reference. This matching process is referred to as "registration". Registering the subsequent anatomical image data to the first anatomical image data can be done by identifying and matching anatomical landmarks. Anatomical landmarks are structures in the subject's anatomy that are know n to have very little or no changes in the time frame of the radiotherapy, such as for example bone structures. The anatomical landmarks can be part of the anatomical image data in the form of contours, e.g. contours of the bone structures that are part of the images. The subsequent anatomical image data is then scaled, translated and rotated until the size and location of the anatomical landmarks corresponds as closely as possible to the size and location of the anatomical landmarks in the first anatomical image data. Preferably this registration is automated.

The analysis unit 111 may further be configured to quantify anatomical changes between the first anatomical image data and the second anatomical image data. This quantification can be absolute, for example the size of the shift of an OAR in millimeters. The quantification can also be relative, for example the percentage a TS has shrunk. In particular, the analysis unit 111 may be further configured to perform the optional additional analysis method steps that will be described below in reference to FIG. 4.

The change state identification unit 112 is configured to identify changes between the first anatomical image data 104 and the subsequent anatomical image data 107 as change states. Change states are a number of predefined categories wherein changes are grouped according to their characteristics. A change state is identified by assigning the category that best corresponds to the characteristics of the change between the first anatomical image data and the subsequent anatomical image data. The change states may be based on categories with characteristics that have been pre-defined by as user, but can also be based on a spatial model or size model. A spatial model defines changes states according to the possible relations between two regions. The number and nature of the change states of the model will depend on the characteristics of interest. The model or models used to identify the change states can be chosen accordingly.

For example, the shift of an ROT may be the characteristic of interest. In this case, changes can be categorized or modelled according to the shifts' size or direction. A well-known model for directions are the compass directions, which define four change states: north, south, east and west. The size of shift can be categorized using ranges defined by the user, for example defining three change states: small, medium and large. In an alternative example, the overlap of an RON with its original position be of interest. A simple overlap model defines four change states: full overlap, partial overlap, touching, and no overlap. In a further alternative example, the change in size of an ROI may be the characteristic of interest. For this example a simple model defines three change states: growth, shrinkage and no change.

The qualitative translator 113 is configured to match the change states that have been identified by the change state identification unit 112 to corresponding qualitative descriptions. Preferably, the qualitative descriptions provide an indication of the characteristics of the change state. For example: "the OAR has shifted left", or "the TS has shrunk". More preferably, the qualitative descriptions reflect how a physician would describe the characteristics of the change when monitoring the patient during treatment. The qualitative translator 113 is preferably configured to match the identified change states to the corresponding qualitative descriptions by using a look-up table. A look-up table provides an easy way of consistently using the same qualitative description for each change state when it is detected.

The reporting unit 114 is configured to provide a monitoring report comprising the qualitative descriptions of the identified change states. In the example of FIG. 1, the reporting unit comprises a display 115 for visually displaying the monitoring report. In a preferred embodiment, the monitoring report is displayed in the form of a graphical user interface, for example the graphical user interface illustrated in FIG. 6.

In the exemplary embodiment illustrated in FIG. 1, the anal sis unit 111 of the system for monitoring anatomical changes 110 additionally comprises an input for receiving dose distribution data 108 of the treatment plan of the subject. This may be the same input that is configured to receive the anatomical image data, but may also be a different input. The dose distribution data preferably comprises delimited dose regions, for example in the form of isodose contours. These delimited dose regions can be used by the system for monitoring anatomical changes in the subject with respect to the planned dose in the place of the first anatomical image data 104. For this purpose, the change state identification unit 112 is preferably further configured to identify changes between the dose distribution data 108 and subsequent anatomical image data 107 as change states. By including this option, the system can additionally or alternatively monitor the anatomical changes in the subject as compared to the planned dose distribution.

In an embodiment of the system for monitoring anatomical changes 110, the change state identification unit 112 comprises at least one qualitative spatial reasoning algorithm, which qualitative spatial reasoning algorithm is preferably an RCC-8 calculus algorithm and/or a Cardinal spatial reasoning algorithm. Qualitative spatial reasoning is an area of artificial intelligence that deals with the problem of generating a qualitative description that summarizes similar quantitative measurements.

Figure 2A:
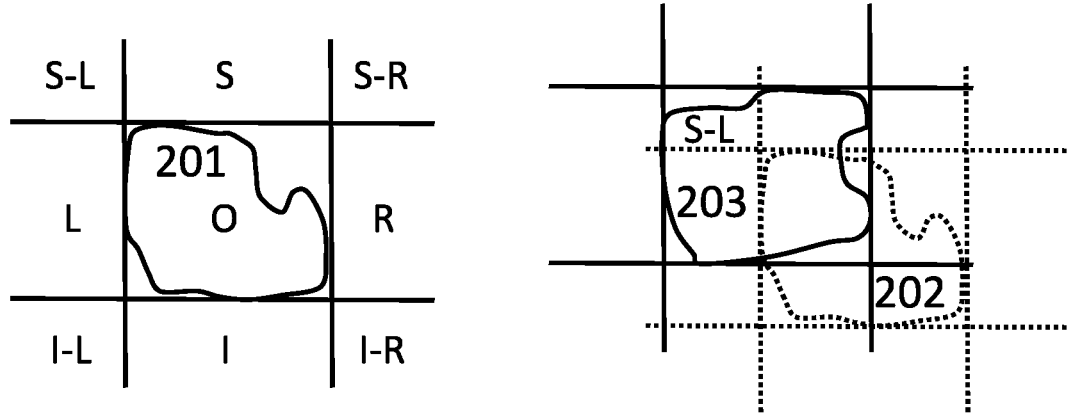
FIGS. 2a and 2b schematically and exemplarily illustrate the detection of states by qualitative spatial reasoning algorithms.
Figure 2B:
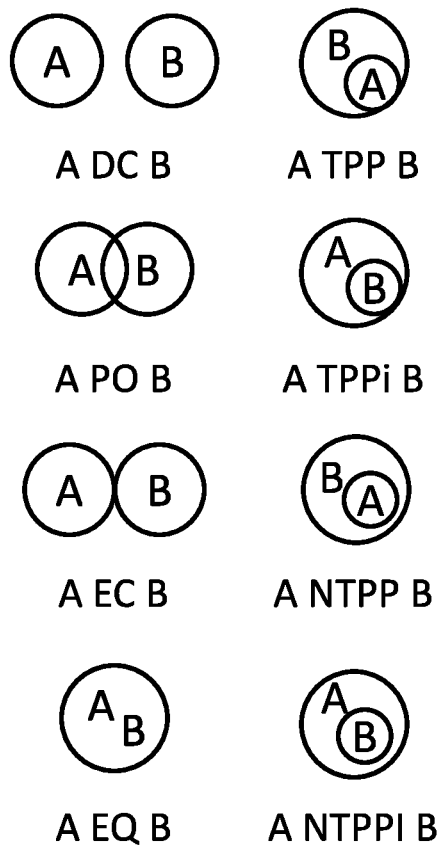

FIGS. 2a and 2b schematically and exemplarily illustrate the detection of change states by qualitative spatial reasoning algorithms.

FIG. 2a illustrates the detection of change states in the form of Cardinal direction relations between two objects. The illustration is for 2D Cardinal spatial reasoning, but this form of modelling can also be used in 3D. 3D Cardinal qualitative spatial reasoning is particularly suitable for detecting and qualitatively describing shifts of ROIs.

As shown in the left side of FIG. 2a, the ROI 201 that forms the basis of the comparison is fitted with a bounding box around which a directional grid is defined. The directional grid forms a model of possible shifted states. The nine change states of this model, here for 2D, are from top to bottom and left to right: upwards and left S-L, left L, downwards and left I-L, upwards S, no shift O, downwards I, upwards and right S-R, right R, and downwards and right I-R.

The right side of FIG. 2a shows the detection of a change state for an ROI. The ROI in the first anatomical image data 202 is shown with dotted contour and grid, and the same ROI is shown in subsequent anatomical image data 203 with solid contour and bounding box. The change state identified is "S-L", which has as corresponding qualitative description in the form of natural language "the ROI has shifted upwards and left".

FIG. 2b illustrates the change states that are identified by RCC-8 calculus. RCC-8 calculus is a type of region connection calculus RCC-8 calculus models the relationship of two regions into eight possible spatial relations that form the change states. RCC-8 calculus can be used for describing changes in a single ROT, but is particularly suitable for describing the position and overlap of TSs and OARs with the high dose areas of the dose distribution of the treatment plan. RCC-8 calculus can also be helpful in describing changes when a TS and an OAR are overlapping or located in close proximity.

The change states of the RCC-8 calculus model are, from top to bottom and left to right in FIG. 2b, disconnected DC, partially overlapping PO, externally connected EC, equal EQ, tangential proper part TPP, tangential proper part inverse TPPi, non-tangential proper part NTPP, and non-tangential proper part NTPPi.

In FIG. 2b, the change states are illustrated for an ROI A and an ROI B. These can be the same ROT, where the first anatomical image data is used for A and the subsequent anatomical image data is used for B. As an example for this, when the change state "A NTPPi B" is identified, this may have the corresponding qualitative description in the form of natural language "the ROI has shrunk". Or, for example, when change state "A DC B" is identified, this may have the corresponding natural language "the ROI has moved fully outside its original location" Alternatively, ROI A can be dose plan data and ROI B can be an ROI of the subsequent image. As an example for this, when change state "A NTTPi B" is identified, this may have the natural language description "The ROI falls within the high dose treatment region" As a further alternative, A and B can also be two different ROIs within the same anatomical image data. For example, A can be an OAR and B a TS. As an example for thus, when change state "A PO B" is detected, this may have the corresponding natural language "the OAR overlaps with the TS".

For the case when there are no changes in the subjects' anatomy, and one or more ROIs are substantially identical in the first and subsequent anatomical image data, this is also identified as a change state. A matching qualitative example description for this state is "no change for ROI". In FIG. 2a this state is detected as "O" and in FIG. 2b this state is detected as "EQ".

Figure 3:
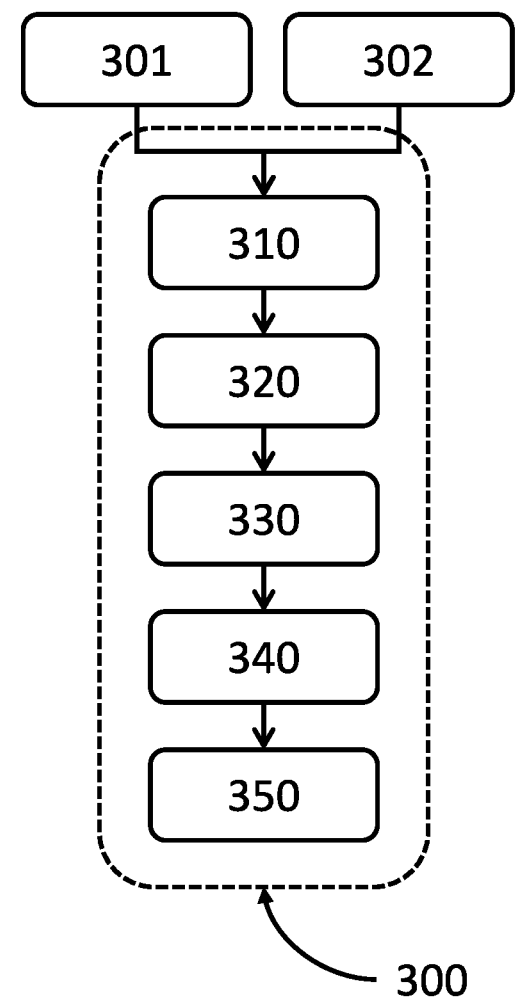
FIG. 3 schematically illustrates an example of a method for monitoring anatomical changes in radiation therapy.

FIG. 3 schematically illustrates steps of a method 300 for monitoring anatomical changes in a subject radiation therapy. The method for monitoring the anatomical changes in the subject is preceded by the steps of obtaining first anatomical image data 301 and subsequent anatomical data 302. This anatomical image data can be obtained in the same manner as described above in relation to the arrangement 100 illustrated in FIG. 1.

The method for monitoring anatomical changes in a subject in radiation therapy 300 according to the invention comprises a step of receiving first anatomical image data and subsequent anatomical image data of the subject 310, and a step of analyzing the first anatomical image data and the subsequent anatomical image data 320, wherein the step of analyzing comprises registering the subsequent anatomical data to the first anatomical data. The method further comprises a step of identifying changes 330 between the first anatomical image data and the subsequent anatomical image data as change states, and a step of matching the identified change states to corresponding qualitative descriptions 340. The method 300 also comprises a step of providing a monitoring report 350 comprising qualitative descriptions of the identified changes.

Figure 4:
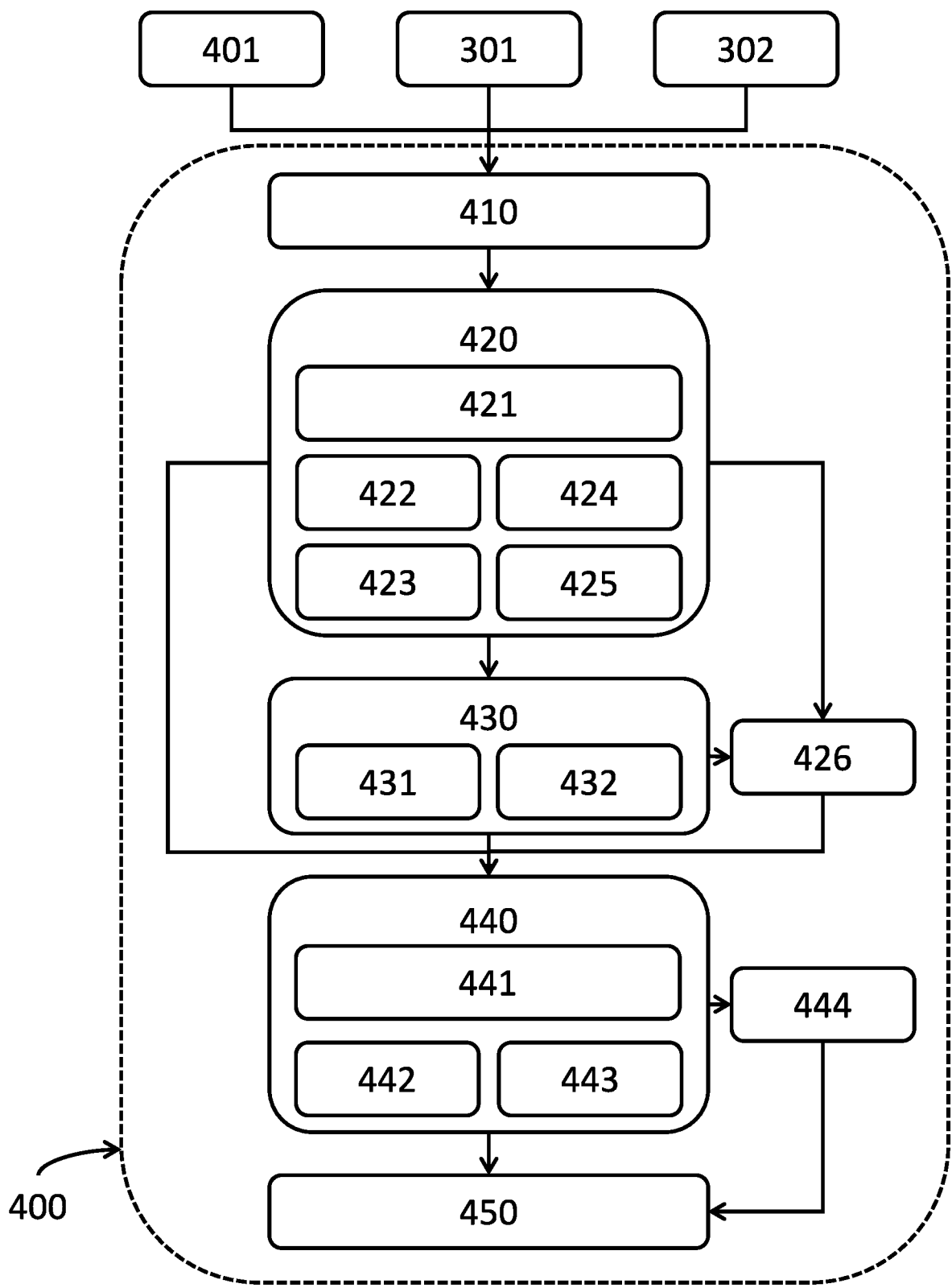
FIG. 4 schematically illustrates another example of a method for monitoring anatomical changes in radiation therapy.

FIG. 4 schematically illustrates steps of another example of a method for monitoring anatomical changes in a subject in radiation therapy 400. The method 400 of FIG. 4 comprises steps 410, 420, 440 and 450 that are analogous to the steps 310, 320, 340 and 350 of the method 300 illustrated in FIG. 3. However, the method steps of FIG. 4 comprise multiple additional options as compared to the method 300 of FIG. 3. These steps represent advantageous additional options that can be used separately, in sub-combinations, or combined in full as illustrated in FIG. 4. Advantageously, the system for monitoring anatomical changes 110 illustrated in FIG. 1 may also be further configured to execute any or all of these additional steps.

The method for monitoring the anatomical changes in the subject is preceded by the steps of obtaining first anatomical image data 301 and subsequent anatomical data 302. The method is also preceded by determining a treatment plan of the subject comprising dose distribution data 401.

The method for monitoring anatomical changes in a subject in radiation therapy 400 according to the invention comprises a step of receiving data 410. This step of receiving data 410 comprises receiving first anatomical image data and subsequent anatomical image data of the subject, and further comprises receiving dose distribution data of the treatment plan of the subject.

The method then comprises a step of analyzing the data 420 that has been received. This step of analyzing the data comprises registering the subsequent anatomical data to the first anatomical data 421. In the exemplary embodiment shown in FIG. 4, the step of analyzing the anatomical image data further comprises obtaining quantitative image data. Obtaining the quantitative data can include any one or more of: determining the size or volume of ROIs 422, the change in size or volume of ROIs 423, the distance ROIs have shifted 424, and/or the radiation dose for the ROIs 425. The ROIs can be one or more OARs and/or one or more TSs. When quantitative data is obtained for changes in ROIs, this can be expressed in absolute value of the changes, but also as a relative value, for example as a percentage.

The method further comprises a step of identifying changes in the received data as change states 430. Changes are identified between the first anatomical image data and the subsequent anatomical image data 431, and are additionally or alternatively identified between the dose distribution data and subsequent anatomical image data 432. In both steps, either the first anatomical image data or the dose distribution data and the subsequent anatomical image data are preferably supplied to one or more spatial reasoning algorithms.

The monitoring method of the exemplary embodiment of FIG. 4 includes an optional step of determining a risk factor 426 for the patient. Quantitative information on the dose an ROI has received is preferably calculated and stored for further reference after delivery of each fraction of the treatment. This information may include a dose volume histogram, a dose distribution in the ROT or an average or total dose received by the entire region of the ROI. Calculating and storing this quantitative dose information has the advantage that the dose an ROI has received to date can be combined with the expected dose that will be delivered in the next fraction based on the subsequent image data. In clinical practice, an ROI has predefined tolerance limits for one or several statistical descriptors of the radiation received that is considered to be safe. These statistical descriptors can be, amongst others, the dose volume histogram, a minimum dose for the entire ROI region, a maximum dose for the entire ROI region, a maximum dose for the hottest sub-region of an ROI, a mean dose, or mean maximum or minimum dose. The appropriate statistical descriptors are determined by the nature of the ROI. For example, for a TS it may be prescribed that at least a minimum dose is delivered in the entire TS region. Also for example, for an OAR it may be prescribed that the mean dose received should not exceed a certain threshold. If the values of the one or more statistical descriptors calculated for the ROI are within predefined tolerance limits, the risk factor will be determined as low. If the values of the one or more statistical descriptors are below the tolerance limits, but are approaching this value, the risk will be determined as medium. If the value of the statistical descriptors for the ROI will exceed the tolerance levels in the next fraction, the risk will be determined as high.

At step 440 of the method, quantitative data obtained from the analysis as well as the identified change states, and the identified risk factor are collected and combined. The identified changes are matched to corresponding descriptions. This step comprises matching the identified changes states to corresponding qualitative descriptions 441. The qualitative descriptions can be supplemented with quantitative data 442, where applicable, as well as the identified risk factor 443. Preferably, quantitative data is used to supplement qualitative natural language descriptions of identified changes, for example "the tumor TS has shrunk by 10%", or "organ OAR has shifted left by 5 mm into the high-dose region". The risk factor determined at 426 can also be indicated separately, for example as "high", "medium", or "low", but can preferably also added to a pictographic qualitative description in the form of a color coding, such as red for high, yellow for medium and green for low. Quantitative data can also be used to supplement pictographic information, for example to illustrate the relative size of the elements of the pictogram.

At step 444 the data that has been collected and combined is further used to identify if the current patient status requires review and follow-up by a physician. For example, if the TS has shifted substantially outside the high dose area of the treatment plan, it may be necessary to revise the treatment plan. In another example, an OAR may have shrunk to an extent that requires additional measures to stabilize the patient and/or reduce adverse side effects of the treatment.

The method also comprises a step of providing a monitoring report 450 comprising qualitative descriptions of the identified changes. In this embodiment quantitative information is also included in the report as well as any follow-up that have been identified at 444 in order to alert the physician to review.

Figure 5:
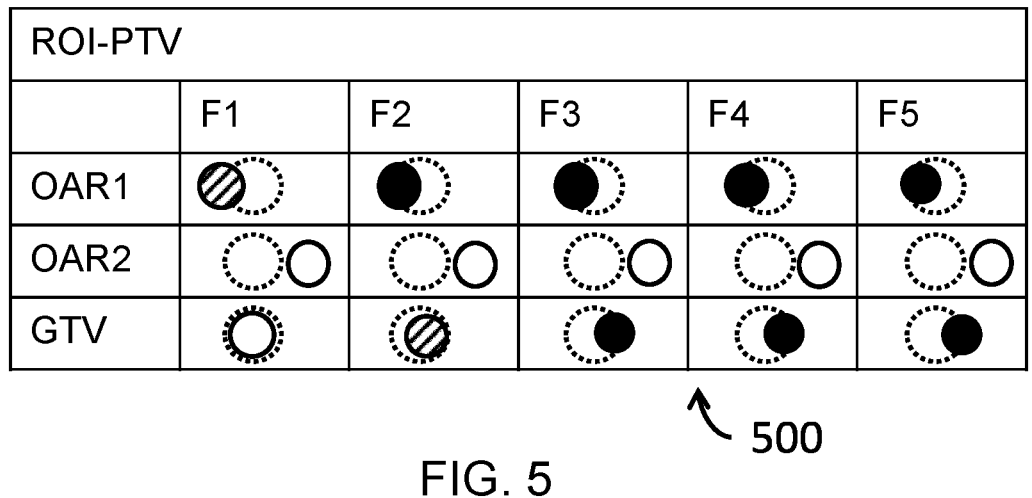
FIG. 5 schematically illustrates an example of a monitoring report of anatomical changes in a subject in the form of a pictographic report.

FIG. 5 schematically illustrates an example of a monitoring report of anatomical changes in a subject in the form of a pictographic report 500. The pictographic report 500 is preferably presented on a display. However, the format also allows hardcopy printing, making it easy to hand out as information to the patient undergoing treatment. In this example the monitoring report 500 is presented in the form of a table. The rows of the table are for the regions of interest that are monitored. In this example the regions of interest are two OARs. OAR1 and OAR2 located in the treatment region and a TS in the form of a tumor GTV. The regions of interest can, for example be the left and right parotid as OARs and a TS in the form of a tumor located close to the left parotid. Columns represents the status of the patient prior to the delivery of a fraction of the treatment. Column F1 is for fraction 1. F2 for fraction 2, etc. The illustrated pictographic report 500 has been provided up to fraction 5. F5. The anatomical changes in this example have been analyzed and reported with respect to the dose distribution of the treatment plan. The dose distribution data consist of the contour of the planned target volume PTV. This is information indicated in the title row of the report ROI-PTV The pictographic report 500 shows change states determined using RCC-8 calculus. The PTV is represented in each pictogram as circle with a dotted contour and each ROI is represented by a circle with a solid contour. Quantitative data has been added in the form of relative size and distance. The pictograms have been further enhanced by a risk indicator in the form of shading. An ROI with low risk has no shading, an ROI with a medium risk hatched shading, and a high risk ROI has solid shading. Alternatively, the colors green, orange and red could be used as a "traffic light" indication of risk. This color scheme is well-known and easily recognizable.

The pictographic report of FIG. 5 can be understood easily not only by the clinician himself, but also by e.g. the patient or a consulting physician from a different field of medicine. For example, for OAR 2 it can be seen that "OAR2 is outside the high dose treatment area, and has a low risk." For example, for OAR1, from F2 to F5 it can be seen that "OAR 1 is shrinking and moving towards that high dose treatment area, this is a high risk situation". As an example for the TS it can be seen that before the delivery of fraction 2 "the tumor has shrunk, but also shifter towards the edge of the high dose treatment area, this represents an increased risk".

In the example of FIG. 5, fractions F3-F4 were delivered in accordance with the original treatment plan. However, in a possible alternative strategy, based on the report provided at setup before delivery of fraction 3, the physician can also decide not to go ahead with the delivery, but instead to acquire a new planning image and to revise the treatment plan for the patient. Having an automated report available that can be provided quickly and that is easily readable, means the setup image acquired from the patient in the treatment room right before delivery can be used for these assessments. Additional imaging for this purpose can be dispensed with.

Figure 6:
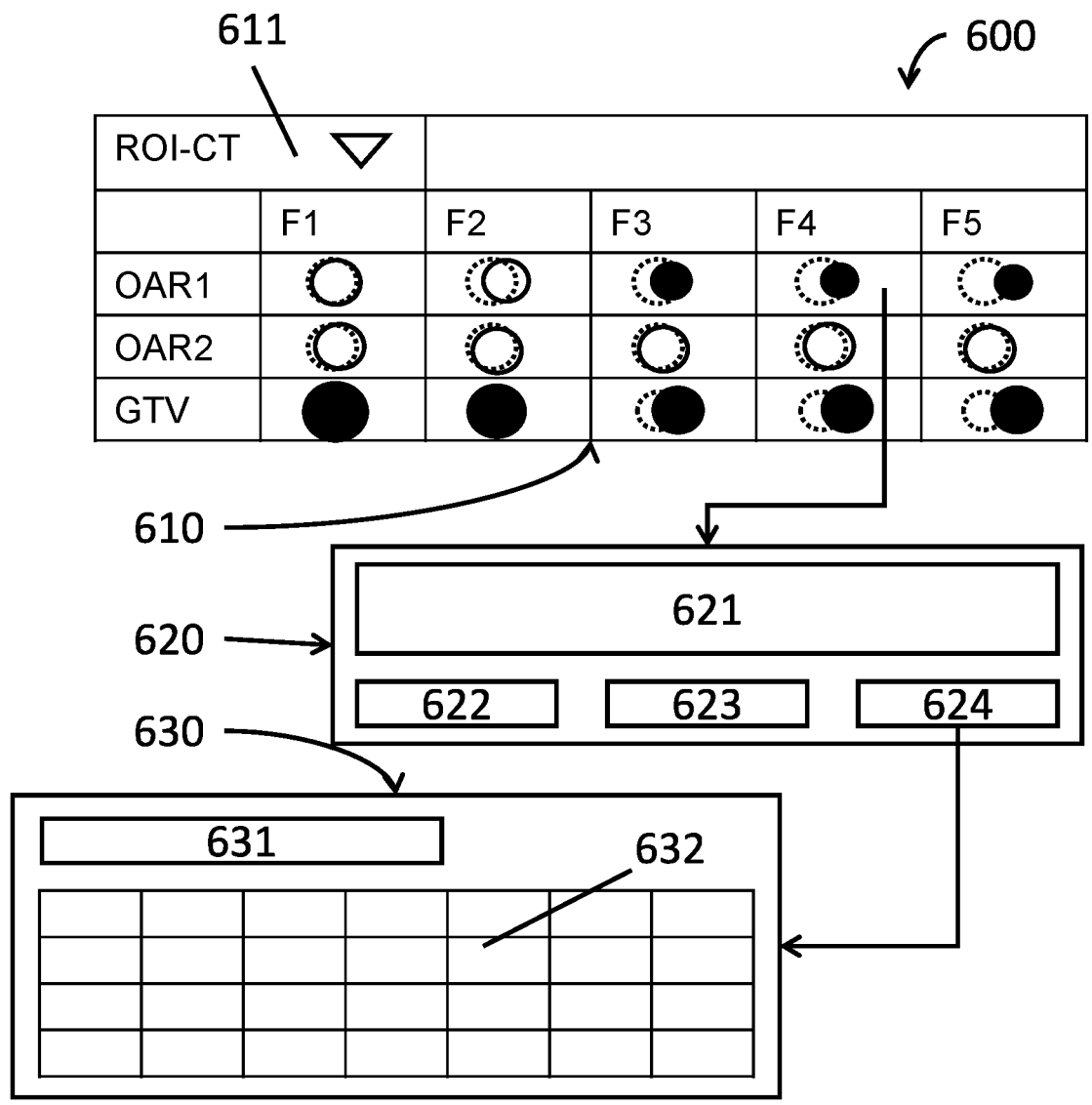
FIG. 6 schematically illustrates another example of a monitoring report of anatomical changes in a subject in the form of a graphic user interface.

FIG. 6 schematically illustrates another example of a monitoring report of anatomical changes in a subject in the form of a graphical user interface (GUI) 600. The report is preferably presented on a display, such as a desktop computer display, presentation screen, or wireless display device. An advantage of presenting the report in the form of a user interface is that a version of the report can be selected and displayed that is most suitable to the situation. A further advantage is that additional data, for example the images acquired of the patient, dosimetric information or quantitative data obtained from further analysis, can be available in the background and accessed and displayed when appropriate or necessary.

In the example of FIG. 6, the main view 610 of the GUI 600 is a pictorgraphic report similar to to pictographic report 500 shown in FIG. 5 and has the same ad vantages. Also here, the rows of the table are for a region of interest that is monitored. In this example the regions of interest again are two OARs, OAR1 and OAR2 located in the treatment region and a TS in the form of a tumor GTV. Columns represents the status of the patient prior to the delivery % of a fraction of the treatment. Column F1 is for fraction 1. F2 for fraction 2, etc. The illustrated pictographic report 500 has been provided up to fraction 5. F5. The pictographic report here again shows change states determined using RCC-8 calculus and supplemented with quantitative data. The first anatomical image data is represented in each pictogram as circle with a dotted contour and subsequent image is represented by a circle with a solid contour. Quantitative data has been added in the form of relative size and distance and the pictograms have been further enhanced by a risk indicator in the form of shading.

The anatomical changes in this example GUI have been analyzed and reported with respect to both the initial image data used for therapy planning and the dose distribution in the treatment plan. The GUI has a view selector in the form of drop down menu 611 that allows the user to choose between the report of the comparison of the subsequent anatomical image data with the dose distribution data, shown as ROI-PTV in FIG. 5, or the comparison of the subsequent anatomical image data with the first anatomical image data, indicated by ROI-CT in FIG. 6. The main view FIG. 6 shows the option where the subsequent anatomical image data of the respective fraction is compared to the first anatomical image data obtained from a planning CT image.

In addition to the example of drop down menu 611, the GUI 600 of FIG. 6 has more controls for selecting the information to be displayed as part of the monitoring report. Each of the pictograms of the data table of main view 610 allows access to further data available for the change state, thereby providing an individual control for each change state. The data can be accessed through, for example, a mouse click on the pictogram, or arrow-key navigation in the table. In the GUI of FIG. 6, a new, additional view 620 is opened when a state is selected. In this example the additional information is shown for the change state of OAR1 as compared to the planning CT prior to the delivery of fraction 4 for the radiation therapy.

Additional view 620 shows the natural language description 621 of the change state supplemented with additional quantitative information, which, for this example, is "GTV increased by 15% and shifted to the right by 5." This provides an easy and consistent understanding of what is shown visually by the pictogram. The natural language description can be used by the physician or clinician in explaining the pictographic report to a patient or co-worker. Additional view 620 also provides further access to more detailed information. In this example access is provided through three controls in the form of three buttons 622, 623 and 624, but more or less buttons are also possible as well as alternative access options such as a drop-down menu.

Button 622 is a "show image" button, configured to open an additional view that shows the subsequent image of the subject. Preferably, the image also shows the anatomical image data in the form of the OAR and TS contours. A particularly advantageous option for this view is to show the subsequent image with its subsequent anatomical image data side by side with the first, planning image with the first anatomical image data. This will allow visual inspection and comparison by the user in case this is desired.

Button 623 is a "dose report" button, configured to open an additional view that shows a dose report. The dose report can be shown in the from of an image, a table, or dose volume histograms. The dose report can also be interactive to allow the user to explore and view multiple forms of dose information.

Button 624 is a "change report" button, configured to open an additional view 630 that shows a change report. The change report provides additional quantitative data on the changes in the subsequent anatomical image data. In the example shown in FIG. 6, the additional view shows the report title 631 and the change report in the form of data table 632.

Any of the method steps disclosed herein, may be recorded in the form of a computer program comprising instructions which when executed on a processor cause the processor to carry out such method steps. The instructions may be stored on a computer program product. The computer program product may be provided by dedicated hardware as well as hardware capable of executing software in association with appropriate software. When provided by a processor the functions can be provided by a single dedicated processor, by a single shared processor or by a plurality of individual processors, some of which can be shared. Furthermore, embodiments of the present invention can take the form of a computer program product accessible from a computer-usable or tangible, non-transitory computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The tangible, non-transitory medium can be an electronic, magnetic, optical, electromagnetic, infrared, or semiconductor system, or apparatus or device, or a propagation medium. Examples of a computer-readable medium include a semiconductor or solid state memory, magnetic tape, a removable computer diskette, a random access memory "RAM", a read-only memory "ROM", a rigid magnetic disk and an optical disk. Current examples of optical disks include compact disk-read only memory "CD-ROM", compact disk-read/write "CD-R/W", Blu-Ray™ and DVD. Examples of a propagation medium are the Internet or other wired or wireless telecommunication systems.

Variations to the disclosed embodiments can be understood and effected by those skilled in the art in practicing the claimed invention, from a study of the drawings, the disclosure, and the appended claims. It is noted that the various embodiments may be combined to achieve further advantageous effects.

In the claims, the word "comprising" does not exclude other elements or steps, and the indefinite article "a" or "an" does not exclude a plurality.

A single unit or device may fulfill the functions of several items recited in the claims. The mere fact that certain measures are recited in mutually different dependent claims does not indicate that a combination of these measures cannot be used to advantage.

Any reference signs in the claims should not be construed as limiting the scope.

The invention claimed is:

1. A system for monitoring anatomical changes in a subject in radiation therapy, the system comprising:
an analysis unit, comprising an input configured to receive first anatomical image data and subsequent anatomical image data of the subject, which analysis unit is at least configured to register the subsequent anatomical data to the first anatomical data;
a change state identification unit configured to identify changes between the first anatomical image data and the subsequent anatomical image data as change states, wherein the change state identification unit comprises at least one qualitative spatial reasoning algorithm;
a qualitative translator configured to match the identified change states to corresponding qualitative descriptions; and
a reporting unit configured to provide a monitoring report comprising qualitative descriptions of the identified change states.

2. The system according to claim 1, wherein the analysis unit further comprises an input configured to receive dose distribution data of a treatment plan of the subject; and the change state identification unit is additionally configured to identify changes between the dose distribution data and subsequent anatomical image data as change states.

3. The system according to claim 1, wherein the qualitative translator is configured to match the identified change states to the corresponding qualitative descriptions by using a look-up table.

4. The system according to claim 1, wherein the corresponding qualitative descriptions are natural language descriptions and/or graphic images.

5. The system according to claim 1, wherein the reporting unit comprises a display configured to visually display the monitoring report.

6. The system according to claim 5, wherein the display is configured to visually display the monitoring report in the form of a graphical user interface.

7. The system according to claim 6, wherein graphical user interface comprises at least one control for selecting the information to be displayed as part of the monitoring report.

8. An arrangement for medical imaging and analysis comprising:
one or more imaging devices configured to provide images of a subject to be treated;
a contouring tool configured to provide anatomical image data based on the images provided by the one or more imaging devices; and
the system of claim 1 for monitoring anatomical changes in a subject in radiation therapy.

9. The system according to claim 1, wherein the qualitative spatial reasoning algorithm is an RCC-8 calculus algorithm and/or a Cardinal spatial reasoning algorithm.

10. The system according to claim 1, wherein the corresponding qualitative descriptions are natural language descriptions and/or graphic image comprise pictograms.

11. A method for monitoring anatomical changes in a subject in radiation therapy, the method comprising:
receiving first anatomical image data and subsequent anatomical image data of the subject;
analyzing the first anatomical image data and the subsequent anatomical image data, wherein analyzing comprises registering the subsequent anatomical data to the first anatomical data;
identifying changes between the first anatomical image data and the subsequent anatomical image data as change states by supplying the first anatomical image data and the subsequent anatomical image data to at least one qualitative spatial reasoning algorithm;
matching the identified change states to corresponding qualitative descriptions; and
providing a monitoring report comprising qualitative descriptions of the identified changes.

12. The method according to claim 11, wherein the receiving first and subsequent anatomical image data of the subject further comprises receiving dose distribution data of a treatment plan of the subject; and wherein the identifying changes additionally or alternatively comprises identifying changes between the dose distribution data and subsequent anatomical image data as change states.

13. The method according to claim 11, wherein the analyzing the anatomical image data further comprises obtaining quantitative image data.

14. The method according to claim 13, wherein the monitoring report further comprises at least one quantitative description of at least one of the identified changes.

15. The method according to claim 13, wherein the analyzing the anatomical image data further comprises obtaining quantitative image data.

16. The method according to claim 13, wherein the quantitative image data comprises at least one of a region of interest size, a region of interest size change, the distance a region of interest has shifted, and the total radiation dose a region of interest has received.

17. The method according to claim 11, herein the qualitative spatial reasoning algorithm is an RCC-8 calculus algorithm and/or a Cardinal spatial reasoning algorithm.

18. A tangible, non-transitory computer readable medium that stores instructions, which when executed by a processor causes the processor to:
    receive first anatomical image data and subsequent anatomical image data of the subject;
    analyze the first anatomical image data and the subsequent anatomical image data, wherein analyzing comprises registering the subsequent anatomical data to the first anatomical data;
    identify changes between the first anatomical image data and the subsequent anatomical image data as change states by supplying the first anatomical image data and the subsequent anatomical image data to at least one qualitative spatial reasoning algorithm;
    match the identified change states to corresponding qualitative descriptions; and
    provide a monitoring report comprising qualitative descriptions of the identified changes.

19. The tangible, non-transitory computer readable medium according to claim 18, wherein when identifying changes, the instructions further cause the processor to supply the first anatomical image data and the subsequent anatomical image data to at least one qualitative spatial reasoning algorithm.

20. The tangible, non-transitory computer readable medium according to claim 19, wherein when the first and subsequent anatomical image data of the subject further are received, the instructions further cause the processor to receive dose distribution data of a treatment plan of the subject.

21. A system for monitoring anatomical changes in a subject in radiation therapy, the system comprising:
    an analysis unit, comprising an input configured to receive first anatomical image data and subsequent anatomical image data of the subject, which analysis unit is at least configured to register the subsequent anatomical data to the first anatomical data;
    a change state identification unit configured to identify changes between the first anatomical image data and the subsequent anatomical image data as change states indicating growth, shrinkage or change of a size of a tumor,
    a qualitative translator configured to match the identified change states to corresponding qualitative descriptions, wherein the qualitative description provides an indication of the characteristics of the change during treatment; and
    a reporting unit configured to provide a monitoring report comprising matching qualitative descriptions of the identified change states.

* * * * *